US009842439B2

(12) United States Patent
Cadotte et al.

(10) Patent No.: US 9,842,439 B2
(45) Date of Patent: Dec. 12, 2017

(54) AIR DATA PROBE CONTAMINATION MONITOR (71) Applicant: Bombardier Inc., Dorval (CA)

(72) Inventors: Patrick Cadotte, Dollard-des-Ormeaux (CA); Sean Lahey, Baie d'Urfe (CA)

(73) Assignee: BOMBARDIER INC., Dorval (CA)

( * ) Notice: Subject to any disclaimer, the term of this patent is extended or adjusted under 35 U.S.C. 154(b) by 0 days.

(21) Appl. No.: 14/910,033

(22) PCT Filed: Jul. 31, 2014

(86) PCT No.: PCT/IB2014/001429
§ 371 (c)(1),
(2) Date: Feb. 4, 2016

(87) PCT Pub. No.: WO2015/019147
PCT Pub. Date: Feb. 12, 2015

(65) Prior Publication Data
US 2016/0180611 A1    Jun. 23, 2016

Related U.S. Application Data (60) Provisional application No. 61/863,473, filed on Aug. 8, 2013.

(51) Int. Cl.
*G07C 5/08* (2006.01)
*G01L 19/00* (2006.01)
(Continued)

(52) U.S. Cl.
CPC ............ *G07C 5/0808* (2013.01); *B64C 13/503* (2013.01); *G01D 5/02* (2013.01);
(Continued)

(58) Field of Classification Search
CPC ........ G01P 5/16; G01P 13/025; G01P 21/025; G07C 5/0808; G07C 5/0816; G01N 25/72;
(Continued)

(56) References Cited

U.S. PATENT DOCUMENTS 5,466,067 A * 11/1995 Hagen ................... G01K 13/02
374/138
6,205,376 B1    3/2001 Gordon
(Continued)

FOREIGN PATENT DOCUMENTS

EP    1008921 A1 *  6/2000 ............. G01C 23/00
EP    1008921 A1 *  6/2000
(Continued)

OTHER PUBLICATIONS

PCT international Search Report and Written Opinion dated Nov. 18, 2014 re: International Application No. PCT/IB2014/001429.
(Continued)

*Primary Examiner* — Atul Trivedi
(74) *Attorney, Agent, or Firm* — Norton Rose Fulbright Canada LLP (57) ABSTRACT

An aircraft air data probe contamination monitor includes at least two air data sensor probes, a first probe located on one side of the aircraft, a second probe located on an opposite side of the aircraft, each probe being operable to generate a parameter value from an airflow passing the in-flight aircraft. The monitor also includes a processor operable to compare the generated parameter value from the first probe to the generated parameter value from the second probe to determine if one of the first probe and the second probe is contaminated.

34 Claims, 2 Drawing Sheets (51) Int. Cl.
*G01L 19/08* (2006.01)
*G01P 13/02* (2006.01)
*G01D 5/02* (2006.01)
*B64C 13/50* (2006.01)
*G01N 25/72* (2006.01)
*G01N 19/08* (2006.01)
*G01P 5/16* (2006.01)
*G01P 21/02* (2006.01)

(52) U.S. Cl.
CPC ........ *G01L 19/0092* (2013.01); *G01L 19/086* (2013.01); *G01N 19/08* (2013.01); *G01N 25/72* (2013.01); *G01P 5/16* (2013.01); *G01P 13/025* (2013.01); *G01P 21/025* (2013.01); *G07C 5/0816* (2013.01)

(58) Field of Classification Search
CPC ....... G01N 19/08; G01L 19/08; G01L 19/086; G01L 19/0092; G01D 5/02; B64C 13/503
USPC ...................................................... 701/30.6
See application file for complete search history.

(56) References Cited

U.S. PATENT DOCUMENTS

| | | | | |
|---|---|---|---|---|
| 7,334,467 | B1* | 2/2008 | DuPuis et al. | G01P 5/165 73/170.02 |
| 8,866,322 | B2* | 10/2014 | Tchoryk, Jr. | G01P 5/26 290/44 |
| 8,930,062 | B2* | 1/2015 | Madhavanpillai | G01P 5/16 701/30.1 |
| 9,038,453 | B2* | 5/2015 | Paris | G01P 5/005 73/170.02 |
| 2008/0147255 | A1* | 6/2008 | Alwin | B64C 13/16 701/14 |
| 2010/0100260 | A1* | 4/2010 | McIntyre | B64C 13/503 701/6 |
| 2011/0208375 | A1* | 8/2011 | Spoerry | G01P 5/16 701/14 |
| 2011/0285550 | A1* | 11/2011 | Maris | G01M 9/065 340/966 |
| 2012/0118037 | A1* | 5/2012 | Leblond | G01P 5/16 73/1.25 |

FOREIGN PATENT DOCUMENTS

EP 1237005 A2 2/2002
EP 1256812 A2 11/2002

OTHER PUBLICATIONS

Collinson, Fly-by-Wire Flight Control, Computing & Control Engineering Journal, Aug. 1999, pp. 141-152, vol. 10, No. 4.
European Patent Office; Office Action dated Feb. 13, 2017 re: European Patent Application No. 14 771 613.8.
European Patent Office, Communication Pursuant to Article 94(3) EPC dated Sep. 21, 2017 re: European Application No. 14 771 613.8.

* cited by examiner

AIR DATA PROBE CONTAMINATION MONITOR

CROSS-REFERENCE TO RELATED APPLICATION(S)

This application is a national phase application under 35 U.S.C. 371 of International Patent Application No. PCT/IB2014/001429 filed on Jul. 31, 2014, which claims priority from U.S. Provisional Patent Application Ser. No. 61/863,473, filed on Aug. 8, 2013, the entire content of which is incorporated herein by reference.

FIELD OF THE INVENTION

The present invention relates in general to a flight control system for an aircraft, and in particular to an aircraft flight control system that includes an air data probe contamination monitor which senses any contamination with the one or more air data sensor probes located on the aircraft, wherein the probe contamination may cause problems with the aircraft when in flight if left undetected.

BACKGROUND OF THE INVENTION

Modern aircraft typically have a number (e.g., four) of air data sensor probes ("ADSPs") usually mounted in the nose portion or aft of the nose portion of the aircraft (e.g. two probes symmetrically located on each side of the tip of the nose portion or aft of the nose portion). These sensor probes sense various characteristics of the airflow passing by the aircraft, including various pressures (e.g., static and dynamic) and temperatures.

Also, modern aircraft commonly use an ADSP that includes a computer or data processor contained within the body or housing of the ADSP. As such, these "self-contained" ADSPs are connected in a "distributed" manner within the aircraft as part of an overall air data system. The ADSPs or the air data system send processed signals indicative of various aircraft characteristics to the flight control computer and/or avionics module on the aircraft for further processing and use for control of the operation of the aircraft. These processed signals may include, among others, the angle of attack and the angle of sideslip of the aircraft in flight, along with aircraft altitude, true and calibrated airspeed, and Mach number. These processed signals are generated by each ADSP from the pressures and temperatures sensed by the ADSPs and are critical to aircraft performance.

Advantages of the self-contained ADSPs include the elimination of the pneumatic tubing required for the older style sensors that did not contain a computer or processor. Other advantages include reduced weight and power consumption, higher reliability, elimination of separate angle of attack transmitters, elimination of separate probe heater current monitors, elimination of skin effects on static measurements, and elimination of pressure lag and pressure checks on the flight line.

However, these self-contained ADSPs are not without their drawbacks. Similar to the older style sensors that did not contain a computer or processor, such newer self-contained ADSPs are also vulnerable or prone to blockage of the pressure ports on the probes by various types of environmental contaminants, such as, for example, icing, ash, insects, liquid ingress, foreign object damage, etc. By its nature, the source of the contamination may affect many, if not all, of the ADSPs. This common cause effect can defeat prior art monitoring strategies relying on comparison of similar signals generated by different air data probes or sensors. It is especially difficult to identify probes with blocked ports when a majority of the ADSPs are contaminated. An air data system with relatively many contaminated ADSPs may generate undetected erroneous data, resulting in potentially catastrophic consequences for the aircraft. For example, the effect of erroneous air data on the aircraft—and on the flight control system in particular—received much attention following the crash of Air France Flight 447. Essentially, it has been shown that modern aircraft are relatively very sensitive to certain types of errors in the air data system.

Known, prior art air data probe contamination monitoring solutions relying on probe to probe comparisons are unable to detect, in every aircraft flight phase, when a majority (or even more than one) of the ADSPs are contaminated. This is particularly true for the modern, fly-by-wire ("FBW") type of aircraft flight control system. Such FBW systems generally include comparison monitoring of air data probe signals to detect and reject a single ADSP failure, and they may also provide for resolution of a generic hardware failure with the air data system. However, a typical FBW system cannot detect the existence of matching erroneous outputs from three or four ADSPs.

It is known to utilize model-based approaches (e.g., in-line reasonableness monitoring) for air data probe contamination monitoring in FBW or other, more classical types of aircraft flight control systems. However, these approaches are relatively complex, are processing intensive, and are unable to cover for every aircraft flight phase.

A FBW flight control system commonly comprises a computer system interposed between: (1) the flight control inputs given both automatically by various aircraft component sensors and subsystems (e.g., the air data system) and manually by the pilots via, e.g., sidestick or yoke controllers, switches, levers, etc.; and (2) the aircraft flight control surfaces and other devices that ultimately control the operation and direction of the aircraft in flight. That is, the inputs from the pilots and the sensors are not connected directly to the aircraft flight control surfaces to be controlled (e.g., ailerons, rudder, elevators, spoilers, slats, flaps, etc.). Instead, the pilot and sensor inputs are routed to a computer system (e.g., typically comprising more than one computer or data processor device for safety redundancy purposes) that contains the flight control logic which interprets the sensor and pilot inputs and outputs flight control surface position commands that move the aircraft flight control surfaces according to control laws ("CLAWS") stored in the computer system to effect changes in the aircraft's pitch, roll, yaw, altitude, etc., for example.

What is needed is an improved aircraft flight control system having an air data probe contamination monitor which senses any contamination with the one or more air data sensor probes located on the aircraft and provides an indication thereof to the aircraft flight control system or avionics module so that corrective action can be taken to avoid a potentially dangerous condition for the aircraft.

SUMMARY OF THE INVENTION

According to an embodiment of the present invention, an air data probe contamination monitor for an aircraft includes at least two air data sensor probes, a first one of the probes being located on one side of the aircraft, a second one of the probes being located on an opposite side of the aircraft, each one of the two probes being operable to generate a parameter value from an airflow passing by the aircraft when the aircraft is in flight. The monitor also includes a processor that is operable to compare the generated parameter value from the first probe to the generated parameter value from the second probe to determine if one of the first probe and the second probe is contaminated.

In an advantageous embodiment of the present invention, the parameter value is generated by sensing an actual pressure from the airflow passing by the aircraft.

In an advantageous embodiment of the present invention, the generated parameter value is an angle of attack value.

In an advantageous embodiment of the present invention, the processor is operable to compare the angle of attack value from the first probe to the angle of attack value from the second probe.

In an advantageous embodiment of the present invention, the generated parameter value is an angle of sideslip value.

In an advantageous embodiment of the present invention, the processor is operable to compare the angle of sideslip value from the first probe to the angle of sideslip value from the second probe.

In an advantageous embodiment of the present invention, the air data probe contamination monitor is part of a flight control system for the aircraft.

In an advantageous embodiment of the present invention, the aircraft flight control system comprises a fly-by-wire type of flight control system.

In an advantageous embodiment of the present invention, the air data probe contamination monitor is part of a flight control system for the aircraft, and if the processor determines that either one or both of the first probe and/or the second probe is contaminated, then the flight control system is notified of the contaminated first probe and/or second probe and/or a flight crew is notified of the contaminated first probe and/or second probe.

In an advantageous embodiment of the present invention, the air data probe contamination monitor further includes at least two vanes, a first one of the vanes being located on one side of the aircraft, a second one of the vanes being located on an opposite side of the aircraft, each one of the two vanes being operable to generate a parameter value from a direction of an airflow passing by the aircraft when the aircraft is in flight, each of the two vanes also being operable to calculate an angle of attack value from the generated parameter value of the direction of the airflow.

In an advantageous embodiment of the present invention, the first probe is located on the same side of the aircraft as the first vane, and the second probe is located on the same side of the aircraft as the second vane.

In an advantageous embodiment of the present invention, the first probe is operable to compare the angle of attack value from the first probe to the angle of attack value from the first vane and to provide a first signal indicative of a result of the first probe/vane comparison, and wherein the second probe is operable to compare the angle of attack value from the second probe to the angle of attack value from the second vane and to provide a second signal indicative of a result of the second probe/vane comparison.

In an advantageous embodiment of the present invention, the processor is responsive to the first probe/vane comparison signal and is responsive to the second probe/vane comparison signal to determine if either one or both of the first probe and/or the second probe is contaminated.

In an advantageous embodiment of the present invention, further including at least one vane being located on the aircraft and being operable to generate a parameter value from a direction of an airflow passing by the aircraft when the aircraft is in flight, the at least one vane also being operable to calculate an angle of attack value from the generated parameter value of the direction of the airflow.

In an advantageous embodiment of the present invention, the at least one vane is located on the same side of the aircraft as one of the first and second probes.

In an advantageous embodiment of the present invention, one of the first probe or second probe is operable to compare the angle of attack value from the at least one vane and to provide a signal indicative of a result of the probe/vane comparison.

In an advantageous embodiment of the present invention, the processor is responsive to the probe/vane comparison signal to determine if either one or both of the first probe and/or the second probe is contaminated.

In an advantageous embodiment of the present invention, further including at least one vane being located on the aircraft and being operable to generate a parameter value from a direction of an airflow passing by the aircraft when the aircraft is in flight, the at least one vane also being operable to calculate an angle of sideslip value from the generated parameter value of the direction of the airflow.

In an advantageous embodiment of the present invention, the at least one vane is located on a top side or a bottom side of the aircraft.

In an advantageous embodiment of the present invention, one of the first probe or second probe is operable to compare the angle of sideslip value from the at least one vane and to provide a signal indicative of a result of the probe/vane comparison.

In an advantageous embodiment of the present invention, the processor is responsive to the probe/vane comparison signal to determine if either one or both of the first probe and/or the second probe is contaminated.

In an advantageous embodiment of the present invention, further including at least two vanes, a first one of the vanes being located on a top side of the aircraft, a second one of the vanes being located on a bottom side of the aircraft, each one of the two vanes being operable to generate a parameter value from a direction of an airflow passing by the aircraft when the aircraft is in flight, each of the two vanes also being operable to calculate an angle of sideslip value from the generated parameter value of the direction of the airflow.

In an advantageous embodiment of the present invention, the first probe is operable to compare the angle of sideslip value from the first probe to the angle of sideslip value from the first vane and to provide a first signal indicative of a result of the first probe/vane comparison, and wherein the second probe is operable to compare the angle of sideslip value from the second probe to the angle of sideslip value from the second vane and to provide a second signal indicative of a result of the second probe/vane comparison.

In an advantageous embodiment of the present invention, the processor is responsive to the first probe/vane comparison signal and is responsive to the second probe/vane comparison signal to determine if either one or both of the first probe and/or the second probe is contaminated.

In an advantageous embodiment of the present invention, the air data probe contamination monitor further includes four air data sensor probes, a first two of the probes being located on one side of the aircraft, a second two of the probes being located on an opposite side of the aircraft, each one of the four probes being operable to generate a parameter value from an airflow passing by the aircraft when the aircraft is in flight, each of the four probes also being operable to calculate one of an angle of attack value and an angle of sideslip value each from the generated parameter value.

In an advantageous embodiment of the present invention, the processor is operable to compare the angle of attack value from each of the first two probes to the angle of attack value from each of the second two probes, and to compare the angle of sideslip value from each of the first two probes to the angle of sideslip value from each of the second two probes to determine if any of the first two probe and/or the second two probes is contaminated.

In an advantageous embodiment of the present invention, the air data probe contamination monitor further includes at least two vanes, a first one of the vanes being located on one side of the aircraft, a second one of the vanes being located on an opposite side of the aircraft, each one of the two vanes being operable to generate a parameter value from a direction of an airflow passing by the aircraft when the aircraft is in flight, each of the two vanes also being operable to calculate an angle of attack value from the generated parameter value, wherein the first two probes are located on the same side of the aircraft as the first vane, and wherein the second two probes are located on the same side of the aircraft as the second vane.

In an advantageous embodiment of the present invention, each of the first two probes is operable to compare the angle of attack value from each of the first two probes to the angle of attack value from the first vane and to provide a pair of first signals each indicative of a result of the first probe/vane comparison, and wherein each of the second two probes is operable to compare the angle of attack value from each of the second two probes to the angle of attack value from the second first vane and to provide a pair of second signals each indicative of a result of the second probe/vane comparison.

In an advantageous embodiment of the present invention, the processor is responsive to the first pair of probe/vane comparison signals and is responsive to the second pair of probe/vane comparison signals to determine if at least one of the first two probes and/or at least one of the second two probes is contaminated.

In an advantageous embodiment of the present invention, further including a third air data sensor probe, the third probe being located on the same side of the aircraft as either one of the at least two probes, the third probe being operable to generate a parameter value from an airflow passing by the aircraft when the aircraft is in flight, the third probe also being operable to calculate one of an angle of attack value and an angle of sideslip value each from the generated parameter value.

In an advantageous embodiment of the present invention, the processor is operable to compare the angle of attack value from the third probe to the angle of attack value from the one of the at least two probes located on the opposite side of the aircraft, and to compare the angle of sideslip value from the third probe to the angle of sideslip value from the one of the at least two probes located on the opposite side of the aircraft to determine if any of the first two probes and/or the third probe is contaminated.

According to another embodiment of the present invention, a method is disclosed for determining if any one of at least two air data sensor probes mounted on opposite sides of an aircraft is contaminated. The method includes each one of the two probes generating a parameter value from an airflow passing by the aircraft while the aircraft is in flight. The method also includes comparing the generated parameter value from the first probe to the generated parameter value from the second probe to determine if one of the first probe and the second probe is contaminated.

In an advantageous embodiment of the present invention, the parameter is generated by sensing an actual pressure from the airflow passing by the aircraft.

In an advantageous embodiment of the present invention, the generated parameter value is an angle of attack value.

In an advantageous embodiment of the present invention, the step of comparing comprises comparing the angle of attack value from the first probe to the angle of attack value from the second probe.

In an advantageous embodiment of the present invention, the generated parameter value is an angle of sideslip value.

In an advantageous embodiment of the present invention, the step of comparing comprises comparing the angle of sideslip value from the first probe to the angle of sideslip value from the second probe.

In an advantageous embodiment of the present invention, if it is determined that either one or both of the first probe and/or the second probe is contaminated, then notifying either an aircraft flight control system and/or a flight crew of the contaminated first and/or second probe.

In an advantageous embodiment of the present invention, at least two vanes are mounted on opposite sides of the aircraft, a first one of the vanes being located on one side of the aircraft, a second one of the vanes being located on an opposite side of the aircraft, the method further including each one of the two vanes generating a parameter value from a direction of an airflow passing by the aircraft when the aircraft is in flight, and each of the two vanes calculating an angle of attack value from the generated parameter value of the direction of the airflow.

In an advantageous embodiment of the present invention, the first probe is located on the same side of the aircraft as the first vane, and wherein the second probe is located on the same side of the aircraft as the second vane.

In an advantageous embodiment of the present invention, further including the first probe comparing the angle of attack value from the first probe to the angle of attack value from the first vane and to provide a first signal indicative of a result of the first probe/vane comparison, and the second probe comparing the angle of attack value from the second probe to the angle of attack value from the second vane and to provide a second signal indicative of a result of the second probe/vane comparison.

In an advantageous embodiment of the present invention, further comprising determining from the first and second signals, if either one or both of the first probe and/or the second probe is contaminated.

In an advantageous embodiment of the present invention, at least one vane being located on the aircraft and generating a parameter value from a direction of an airflow passing by the aircraft when the aircraft is in flight, and calculating an angle of attack value from the generated parameter value of the direction of the airflow.

In an advantageous embodiment of the present invention, the at least one vane is located on the same side of the aircraft as one of the first and second probes.

In an advantageous embodiment of the present invention, one of the first probe or second probe compares the angle of attack value from the at least one vane and provides a signal indicative of a result of the probe/vane comparison.

In an advantageous embodiment of the present invention, further comprising determining from the probe/vane comparison signal if either one or both of the first probe and/or the second probe is contaminated.

In an advantageous embodiment of the present invention, at least one vane being located on the aircraft and generating a parameter value from a direction of an airflow passing by the aircraft when the aircraft is in flight, and calculating an angle of sideslip value from the generated parameter value of the direction of the airflow.

In an advantageous embodiment of the present invention, the at least one vane is located on a top side or a bottom side of the aircraft.

In an advantageous embodiment of the present invention, one of the first probe or second probe compares the angle of sideslip value from the at least one vane and provides a signal indicative of a result of the probe/vane comparison.

In an advantageous embodiment of the present invention, further comprising determining from the probe/vane comparison signal if either one or both of the first probe and/or the second probe is contaminated.

In an advantageous embodiment of the present invention, wherein at least two vanes are located on the aircraft, a first one of the vanes being located on a top side of the aircraft, a second one of the vanes being located on a bottom side of the aircraft, each one of the two vanes generating a parameter value from a direction of an airflow passing by the aircraft when the aircraft is in flight, and calculating an angle of sideslip value from the generated parameter value of the direction of the airflow.

In an advantageous embodiment of the present invention, wherein the first probe compares the angle of sideslip value from the first probe to the angle of sideslip value from the first vane and provides a first signal indicative of a result of the first probe/vane comparison, and the second probe compares the angle of sideslip value from the second probe to the angle of sideslip value from the second vane and provides a second signal indicative of a result of the second probe/vane comparison.

In an advantageous embodiment of the present invention, further comprising determining, in response to the first probe/vane comparison signal and to the second probe/vane comparison signal, if either one or both of the first probe and/or the second probe is contaminated.

In an advantageous embodiment of the present invention, further including four air data sensor probes, a first two of the probes being located on one side of the aircraft, a second two of the probes being located on an opposite side of the aircraft. The method further includes each one of the four probes generating a parameter value from an airflow passing by the aircraft when the aircraft is in flight, each of the four probes calculating one of an angle of attack value and an angle of sideslip value from the generated parameter value.

In an advantageous embodiment of the present invention, further including comparing the angle of attack value from each of the first two probes to the angle of attack value from each of the second two probes, and comparing the angle of sideslip value from each of the first two probes to the angle of sideslip value from each of the second two probes to determine if any of the first two probe and/or the second two probes is contaminated.

In an advantageous embodiment of the present invention, further including at least two vanes, a first one of the vanes being located on one side of the aircraft, a second one of the vanes being located on an opposite side of the aircraft. The method further includes each one of the two vanes generating a parameter value from a direction of an airflow passing by the aircraft when the aircraft is in flight, each of the two vanes calculating an angle of attack value from the sensed actual pressure parameter value, wherein the first two probes are located on the same side of the aircraft as the first vane, and wherein the second two probes are located on the same side of the aircraft as the second vane.

In an advantageous embodiment of the present invention, further including comparing the angle of attack value from each of the first two probes to the angle of attack value from the first vane and providing a pair of first signals each indicative of a result of the first probe/vane comparison. Also, comparing the angle of attack value from each of the second two probes to the angle of attack value from the second first vane and providing a pair of second signals each indicative of a result of the second probe/vane comparison.

In an advantageous embodiment of the present invention, further including determining, in response to the first pair of probe/vane comparison signals and to the second pair of probe/vane signals, if at least one of the first two probes and/or at least one of the second two probes is contaminated.

In an advantageous embodiment of the present invention, further comprising a third air data sensor probe, the third probe being located on the same side of the aircraft as either one of the at least two probes, the third probe generating a parameter value from an airflow passing by the aircraft when the aircraft is in flight and calculating one of an angle of attack value and an angle of sideslip value each from the generated parameter value.

In an advantageous embodiment of the present invention, further comprising comparing the angle of attack value from the third probe to the angle of attack value from the one of the at least two probes located on the opposite side of the aircraft, and comparing the angle of sideslip value from the third probe to the angle of sideslip value from the one of the at least two probes located on the opposite side of the aircraft to determine if any of the first two probes and/or the third probe is contaminated.

According to yet another embodiment of the present invention, a computer program product is disclosed for determining if any one of at least two air data sensor probes mounted on opposite sides of an aircraft is contaminated. The computer program product includes each one of the two probes generating a parameter value from an airflow passing by the aircraft while the aircraft is in flight. The computer program product also includes comparing the generated parameter value from the first probe to the generated parameter value from the second probe to determine if one of the first probe and the second probe is contaminated.

In an advantageous embodiment of the present invention, the parameter is generated by sensing an actual pressure from the airflow passing by the aircraft.

In an advantageous embodiment of the present invention, the generated parameter value is an angle of attack value.

In an advantageous embodiment of the present invention, the step of comparing comprises comparing the angle of attack value from the first probe to the angle of attack value from the second probe.

In an advantageous embodiment of the present invention, the generated parameter value is an angle of sideslip value.

In an advantageous embodiment of the present invention, the step of comparing comprises comparing the angle of sideslip value from the first probe to the angle of sideslip value from the second probe.

In an advantageous embodiment of the present invention, if it is determined that either one or both of the first probe and/or the second probe is contaminated, then notifying either an aircraft flight control system and/or a flight crew of the contaminated first and/or second probe.

In an advantageous embodiment of the present invention, at least two vanes are mounted on opposite sides of the aircraft, a first one of the vanes being located on one side of the aircraft, a second one of the vanes being located on an opposite side of the aircraft, the method further including each one of the two vanes generating a parameter value from a direction of an airflow passing by the aircraft when the aircraft is in flight, and each of the two vanes calculating an angle of attack value from the generated parameter value of the direction of the airflow.

In an advantageous embodiment of the present invention, the first probe is located on the same side of the aircraft as the first vane, and wherein the second probe is located on the same side of the aircraft as the second vane.

In an advantageous embodiment of the present invention, further including the first probe comparing the angle of attack value from the first probe to the angle of attack, value from the first vane and to provide a first signal indicative of a result of the first probe/vane comparison, and the second probe comparing the angle of attack value from the second probe to the angle of attack value from the second vane and to provide a second signal indicative of a result of the second probe/vane comparison.

In an advantageous embodiment of the present invention, further comprising determining from the first and second signals, if either one or both of the first probe and/or the second probe is contaminated.

In an advantageous embodiment of the present invention, at least one vane being located on the aircraft and generating a parameter value from a direction of an airflow passing by the aircraft when the aircraft is in flight, and calculating an angle of attack value from the generated parameter value of the direction of the airflow.

In an advantageous embodiment of the present invention, the at least one vane is located on the same side of the aircraft as one of the first and second probes.

In an advantageous embodiment of the present invention, one of the first probe or second probe compares the angle of attack value from the at least one vane and provides a signal indicative of a result of the probe/vane comparison.

In an advantageous embodiment of the present invention, further comprising determining from the probe/vane comparison signal if either one or both of the first probe and/or the second probe is contaminated.

In an advantageous embodiment of the present invention, at least one vane being located on the aircraft and generating a parameter value from a direction of an airflow passing by the aircraft when the aircraft is in flight, and calculating an angle of sideslip value from the generated parameter value of the direction of the airflow.

In an advantageous embodiment of the present invention, the at least one vane is located on a top side or a bottom side of the aircraft.

In an advantageous embodiment of the present invention, one of the first probe or second probe compares the angle of sideslip value from the at least one vane and provides a signal indicative of a result of the probe/vane comparison.

In an advantageous embodiment of the present invention, further comprising determining from the probe/vane comparison signal if either one or both of the first probe and/or the second probe is contaminated.

In an advantageous embodiment of the present invention, wherein at least two vanes are located on the aircraft, a first one of the vanes being located on a top side of the aircraft, a second one of the vanes being located on a bottom side of the aircraft, each one of the two vanes generating a parameter value from a direction of an airflow passing by the aircraft when the aircraft is in flight, and calculating an angle of sideslip value from the generated parameter value of the direction of the airflow.

In an advantageous embodiment of the present invention, wherein the first probe compares the angle of sideslip value from the first probe to the angle of sideslip value from the first vane and provides a first signal indicative of a result of the first probe/vane comparison, and the second probe compares the angle of sideslip value from the second probe to the angle of sideslip value from the second vane and provides a second signal indicative of a result of the second probe/vane comparison.

In an advantageous embodiment of the present invention, further comprising determining, in response to the first probe/vane comparison signal and to the second probe/vane comparison signal, if either one or both of the first probe and/or the second probe is contaminated.

In an advantageous embodiment of the present invention, further including four air data sensor probes, a first two of the probes being located on one side of the aircraft, a second two of the probes being located on an opposite side of the aircraft. The method further includes each one of the four probes generating a parameter value from an airflow passing by the aircraft when the aircraft is in flight, each of the four probes calculating one of an angle of attack value and an angle of sideslip value each from the sensed generated parameter value.

In an advantageous embodiment of the present invention, further including comparing the angle of attack value from each of the first two probes to the angle of attack value from each of the second two probes, and comparing the angle of sideslip value from each of the first two probes to the angle of sideslip value from each of the second two probes to determine if any of the first two probe and/or the second two probes is contaminated.

In an advantageous embodiment of the present invention, further including at least two vanes, a first one of the vanes being located on one side of the aircraft, a second one of the vanes being located on an opposite side of the aircraft. The method further includes each one of the two vanes generating a from a direction of an airflow passing by the aircraft when the aircraft is in flight, each of the two vanes calculating an angle of attack value from the sensed actual pressure parameter value, wherein the first two probes are located on the same side of the aircraft as the first vane, and wherein the second two probes are located on the same side of the aircraft as the second vane.

In an advantageous embodiment of the present invention, further including comparing the angle of attack value from each of the first two probes to the angle of attack value from the first vane and providing a pair of first signals each indicative of a result of the first probe/vane comparison. Also, comparing the angle of attack value from each of the second two probes to the angle of attack value from the second first vane and providing a pair of second signals each indicative of a result of the second probe/vane comparison.

In an advantageous embodiment of the present invention, further including determining, in response to the first pair of probe/vane comparison signals and to the second pair of probe/vane signals, if at least one of the first two probes and/or at least one of the second two probes is contaminated.

In an advantageous embodiment of the present invention, further comprising a third air data sensor probe, the third probe being located on the same side of the aircraft as either one of the at least two probes, the third probe generating a parameter value from an airflow passing by the aircraft when the aircraft is in flight and calculating one of an angle of attack value and an angle of sideslip value each from the generated parameter value.

In an advantageous embodiment of the present invention, further comprising comparing the angle of attack value from the third probe to the angle of attack value from the one of the at least two probes located on the opposite side of the aircraft, and comparing the angle of sideslip value from the third probe to the angle of sideslip value from the one of the at least two probes located on the opposite side of the aircraft to determine if any of the first two probes and/or the third probe is contaminated.

Embodiments of the present invention provide for a relatively simple air data probe contamination monitor which uses known or validated characteristics of various signals, while at the same time not being overly reliant on behavioral models. These signals may be provided by modern, self-contained ADSPs having both a sensor and a computer or processor located within a housing of the ADSP, or may be provided by the older, more classical type of system that uses pressure sensing devices without a computer or processor directly associated with the pressure sensing devices in a self-contained manner. Also, aircraft with a modern fly-by-wire type of flight control system, or aircraft having a classical flight control system can benefit from embodiments of the present invention. In addition, existing aircraft may have embodiments of the present invention adapted thereto through a retrofitting process.

BRIEF DESCRIPTION OF THE DRAWINGS

The various embodiments of the present invention can be understood with reference to the following drawings. The components are not necessarily to scale. Also, in the drawings, like reference numerals designate corresponding parts throughout the several views.

DETAILED DESCRIPTION OF THE INVENTION

The present invention is more particularly described in the following description and examples that are intended to be illustrative only since numerous modifications and variations therein will be apparent to those skilled in the art. As used in the specification and in the claims, the singular form "a," "an," and "the" may include plural referents unless the context clearly dictates otherwise. Also, as used in the specification and in the claims, the term "comprising" may include the embodiments "consisting of" and "consisting essentially of." Furthermore, all ranges disclosed herein are inclusive of the endpoints and are independently combinable.

As used herein, approximating language may be applied to modify any quantitative representation that may vary without resulting in a change in the basic function to which it is related. Accordingly, a value modified by a term or terms, such as "about" and "substantially," may not to be limited to the precise value specified, in some cases. In at least some instances, the approximating language may correspond to the precision of an instrument for measuring the value.

In embodiments of the present invention, an air data probe contamination monitor for an aircraft includes at least two air data sensor probes, a first one of the probes being located on one side of the aircraft, a second one of the probes being located on an opposite side of the aircraft, each one of the two probes being operable to generate a parameter value from an airflow passing by the aircraft when the aircraft is in flight. The monitor also includes a processor that is operable to compare the parameter value from the first probe to the parameter value from the second probe to determine if one of the first probe and the second probe is contaminated.

The foregoing and other features of various disclosed embodiments of the invention will be more readily apparent from the following detailed description and drawings of the illustrative embodiments of the invention wherein like reference numbers refer to similar elements.

Figure 1:
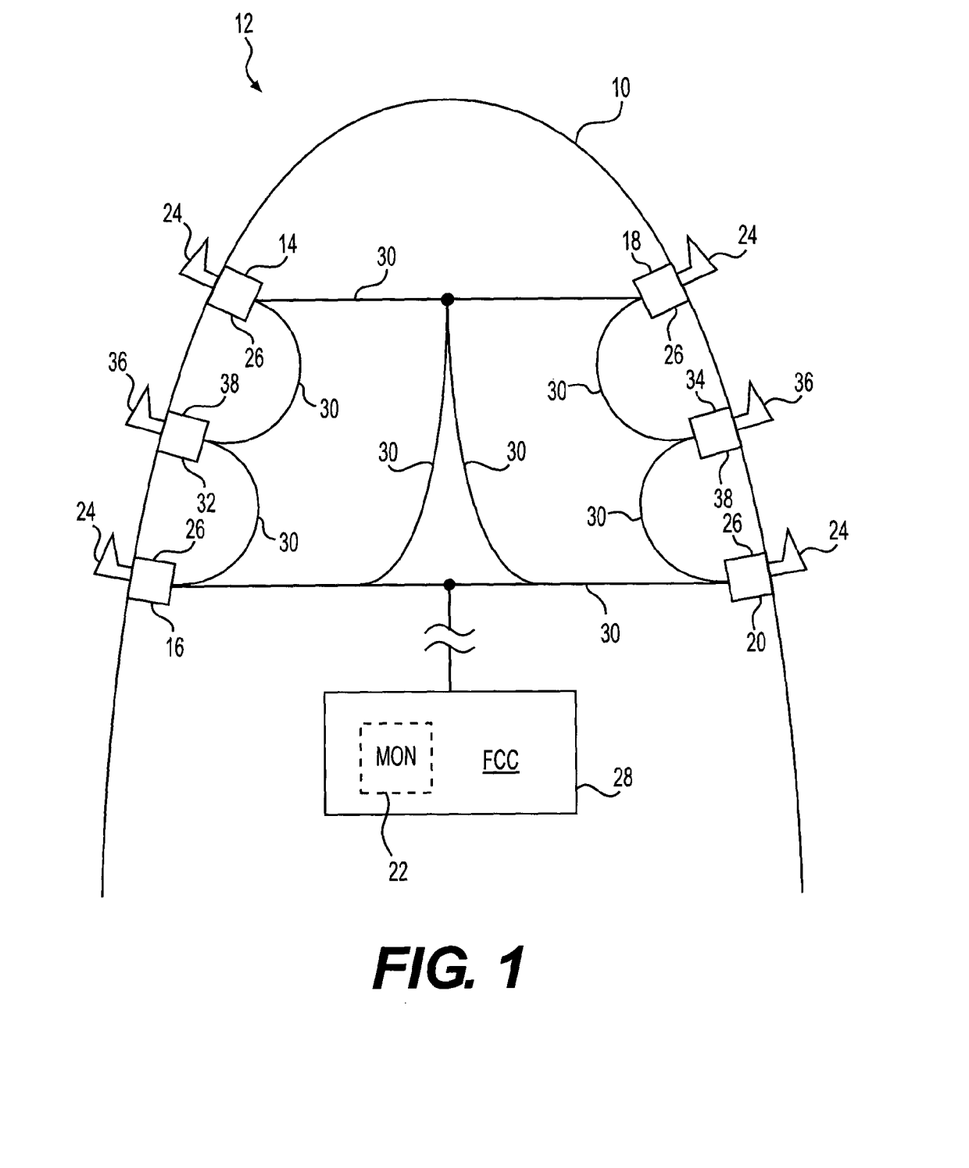
FIG. 1 is schematic diagram of a nose portion of an aircraft having a number of ADSPs and an air data probe contamination monitor in accordance with embodiments of the present invention.

Referring to FIG. 1, there illustrated is a schematic diagram of a nose portion 10 of an aircraft 12 having a number of air data sensor probes ("ADSPs") 14-20 and an air data probe contamination monitor 22 in accordance with embodiments of the present invention. Two of the ADSPs 14, 16 are located on one side of the aircraft 12 and are designated ADSP #1 14 and ADSP #3 16. The other two of the ADSPs 18, 20 are located on the opposite side of the aircraft 12 and are designated ADSP #2 18 and ADSP #4 20. However, it is to be understood that the ADSPs 14-20 and/or the monitor 22 being mounted near the nose portion 10 of the aircraft 12 is purely exemplary. Instead, the ADSPs 14-20 and/or the monitor 22 may be mounted in a location aft of the nose portion 10 of the aircraft 12, or in some other appropriate location on the aircraft, as should be apparent to one of ordinary skill in the art in light of the teachings herein.

As is known, each ADSP 14-20 has a number of pressure ports in the form of, e.g., notches, located on a sensing probe portion 24 that protrudes out into the airstream passing by the aircraft 12 when in flight. These pressure ports typically measure, sense or generate various parameters such as pressures in the airstream from which can be deduced flight parameters such as angle of attack, angle of sideslip, static pressure, pitot pressure, airspeed, and altitude. These various aircraft flight parameters may be calculated in known manner by a computer or processor located within the housing 26 of each ADSP 14-20. Thus, each ADSP 14-20 may be considered to be a self-contained air data computer or system.

The four ADSPs 14-20 may be connected with one another and with a flight control computer ("FCC") 28 or aircraft avionics module 28 by signal wires 30. The flight control computer or avionics module 28 may contain the air data probe contamination monitor 22 in embodiments of the present invention. Instead, the monitor 22 may be a stand-alone device or module apart from the flight control computer or avionics module 28. Regardless, in embodiments of the present invention, the air data probe contamination monitor 22 may comprise software that runs on a computer or processor that is part of the flight control computer or avionics module 28. However, it is to be understood that various other embodiments of the present invention contemplate that the air data probe contamination monitor 22 be embodied entirely in electronic hardware, or partly in software and partly in hardware. Also the flight control computer or avionics module 28 may be part of a fly-by-wire ("FBW") type of aircraft flight control system. In the alternative, the flight control computer or avionics module 28 may be part of a more traditional or "classical" mechanical or hydro-mechanical type of aircraft flight control system.

According to embodiments of the present invention, FIG. 1 also illustrates two vanes 32, 34—one vane 32 being designated vane #1 32 and disposed on one side of the aircraft 12 having ADSP #1 14 and ADSP #3 16; the other vane 32 being designated vane #2 34 and disposed on the other side of the aircraft 12 having ADSP #2 18 and ADSP #4 20. Each vane 32, 34 has a sensing portion 36 that protrudes out into the airstream passing by the aircraft 12 when in flight, along with a computer or processor located within the housing 38 of each vane 32, 34. Also, each vane 32, 34 may communicate with the ADSPs 14-20 and the air data probe contamination monitor 22 by signal wires 30. In the alternative, each vane 32, 34 may communicate instead directly and only with the FCC or avionics module 28. As will become more apparent hereinafter, each vane 32, 34 provides a secondary indication of the angle of attack of the aircraft 12 to the air data probe contamination monitor 22 (or to the FCC or avionics module 28), which may be utilized in embodiments of the present invention as discussed hereinafter. Further, in accordance with alternative embodiments of the present invention and as described in more detail hereinafter, only one of the vanes 32, 34 may be utilized instead of the two vanes 32, 34 illustrated in FIG. 1.

Figure 2:
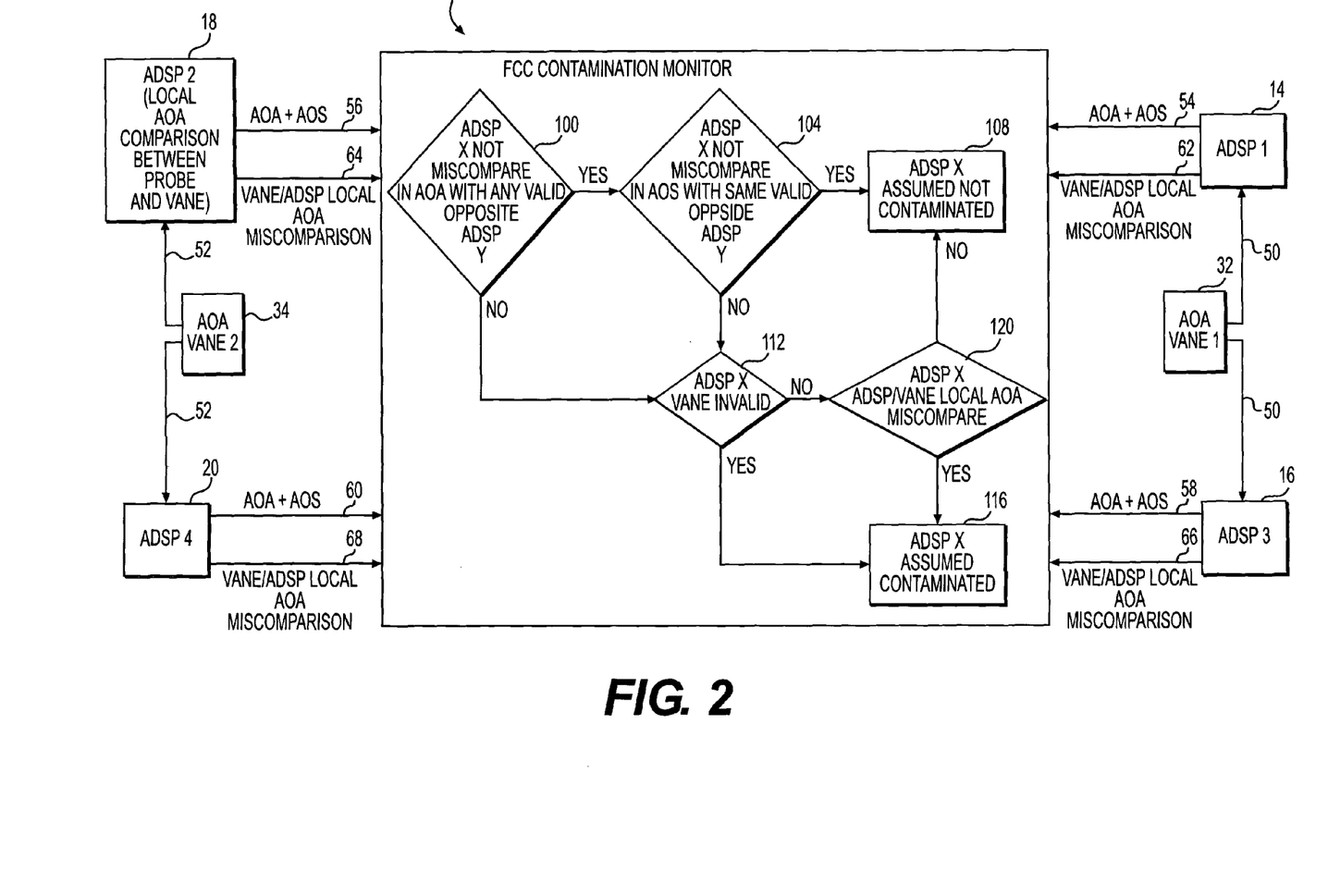
FIG. 2 is a detailed block diagram of the ADSPs and vanes of FIG. 1, along with a detailed logic diagram of the air data probe contamination logic in accordance with an embodiment of the present invention.

Referring to FIG. 2, there illustrated in more detail in block diagram form are the ADSPs 14-20 and the two vanes 32, 34, along with a detailed logic diagram description of the air data probe contamination logic 22 in accordance with an embodiment of the present invention. As discussed hereinabove, this logic 22 may be embodied in software and executed by the flight control computer 28 of FIG. 1. Thus, FIG. 2 may also function as a flowchart of steps in a method executed by the processor that embodies the air data probe contamination logic 22 according to embodiments of the present invention.

According to embodiments of the present invention and as mentioned hereinabove, each of the ADSPs 14-20 senses or generates various pressures and temperatures from the airflow passing by the aircraft in the vicinity of the ADSPs 14-20 and calculates various aircraft flight parameters therefrom. For example, each ADSP 14-20 calculates an angle of attack ("AOA") value. Also each of the two vanes 32, 34 also calculates an angle of attack value from the pressures that it senses in the airflow passing by the aircraft 12 while in flight. Vane #1 32 provides its calculated AOA value to both of ADSP #1 14 and ADSP #3 16 on signal lines 50. Vane #2 34 provides its calculated AOA value to both of ADSP #2 18 and ADSP #4 20 on signal lines 52.

In the alternative and as mentioned hereinabove, the vanes 32, 34 may instead communicate solely with the FCC or avionics module 28 and not the air date probe contamination logic 22. As such, the portion of the logic 22 described herein involving the vanes 32, 34 may instead be executed by the FCC or the avionics module 28. Such logic executed by the FCC or avionics module 28 may be similar to that described herein or may differ to some extent but if different, such differences should be apparent to one of ordinary skill in the art in light of the teachings herein.

Each ADSP 14-20 provides a signal on a line 54-60, respectively, to the air data probe contamination monitor logic 22, wherein each of these signals 54-60 is indicative of both the AOA calculated by the corresponding ADSP 14-20 and is also indicative of the angle of sideslip ("AOS") of the aircraft 12 while in flight as calculated by each of the ADSPs 14-20.

Also, each ADSP 14-20 also calculates an amount of difference (i.e., "miscomparison") between the AOA value calculated by each ADSP 14-20 and the AOA value calculated by each vane 32, 34. Each ADSP 14-20 then provides a signal on a line 62-68, respectively, indicative of the amount of difference or "miscomparison" between the two AOA values. Each signal on the lines 62-68 may be indicative of a binary "flag" in which the flag may be set to a binary "one" or "true" value if the amount of difference between the ADSP AOA value and the vane AOA value differs by a predetermined amount for a certain period of time. Otherwise this binary "flag" may be set to binary "zero" or "false" value.

As shown in FIG. 2, the logic 22 within the flight control computer or avionics module 28 (FIG. 1) may then "start" by checking in a step 100 if each ADSP 14-20 on one side of the aircraft 12 "agrees" with each of the ADSPs 14-20 on the other side of the aircraft 12. In an embodiment of the present invention, the step 100 does this by checking for "agreement" of the AOA values calculated by each ADSP 14-20, and not including the AOA value calculated by the vanes 32, 34 and provided to the corresponding ADSPs 14-20. An ADSP 14-20 is in "agreement" with an opposite side ADSP 14-20 using one or more of various criteria—for example, an amount of degrees of the AOA angle, if the two ADSP AOA values are within a certain number of degrees.

An example of the logic of step 100 is that the ADSP #1 14 on one side of the aircraft 12 checks its AOA value against the AOA value of the ADSP #2 18 on the other side of the aircraft 12. If the two AOA values compare favorably (i.e., are within a certain number of degrees), then a step 104 is executed in which the AOS value from ADSP #1 14 is compared to the AOS value from ADSP #2 18 on the other side of the aircraft. The criterion used by the step 104 to determine if the two AOS values are in agreement may be a number of degrees of difference between the two AOS values not being exceeded. If, as a result of the step 104, the two AOS values are in "agreement," then ADSP #1 14 is assumed to not be contaminated in a step 108.

Returning to step 100, if the AOA value of ADSP #1 14 is not in agreement with the AOA value from ADSP #2 18, then a step 112 is executed in which ADSP #1 14 is checked to see if it is invalid. This may be indicated by a validity bit or an indicator of some type included with the AOA value from the ADSP #1 14. If the ADSP #1 14 is determined to be invalid in the step 112, then a step 116 is executed in which ADSP #1 may be assumed to be contaminated. As such, the flight control computer or avionics module 28 on the aircraft 12 may stop using any AOA or AOS values from ADSP #1 14. Although this rule may not be strictly true. In alternative embodiments, a single ADSP 14-20 being contaminated, or two ADSPs 14-20 being contaminated, may instead be determined not to be a problematic situation for the aircraft 12. Instead, it is only when at least three ADSPs 14-20 are contaminated is there considered to be a problem.

If, instead, the step 112 determines that the ADSP #1 14 is valid, then a step 120 is executed in which the signal on the line 54 is checked to see if the AOA value calculated locally by the ADSP #1 14 compared favorably or was in agreement with the AOA value provided by the vane #1 32. As described hereinbefore, this comparison takes place within the ADSP #1 14 itself and the result of the comparison is indicated by a binary value on the signal line 62.

If the ADSP #1 14 AOA value is not in agreement with the AOA value from the vane #1 32, then the step 116 is executed in which the ADSP #1 14 is assumed to be contaminated.

Instead, if the ADSP #1 14 AOA value is in agreement with the AOA value from the vane #1 32, then the step 108 is executed in which ADSP #1 14 is assumed to be not contaminated.

The steps 100-120 are repeated for ADSP #1 14 as compared to ADSP #4 20, since ADSP #4 is located on the opposite side of the aircraft 12 from ADSP #1 14. Similarly, the steps 100-120 are repeated for ADSP #3 16 as compared to each of ADSP #2 18 and ADSP #4 20, since ADSP #3 16 is on the opposite side of the aircraft from ADSP #2 18 and ADSP #4 20.

In accordance with embodiments of the present invention, the steps 100-120 are repeated for each of ADSP #2 18 as compared to each of ADSP #1 14 and ADSP #3 16, and are also repeated for each of ADSP #4 20 as compared to each of ADSP #1 14 and ADSP #3 16. This is because ADSP #2 18 and ADSP #4 20 are each on the opposite side of the aircraft 12 from ADSP #1 14 and ADSP #3 16.

The reason that ADSPs 14-20 on one side of the aircraft 12 are compared with the ADSPs 14-20 on the other side of the aircraft 12 is that the two ADSPs 14-20 on either side of the aircraft 12 tend to exhibit the same AOA and AOS errors because they are on the same side of the aircraft 12.

Thus, in embodiments of the present invention, a single "not contaminated" confirmation between two opposite side ADSPs 14-20 indicates a "not contaminated" condition of both of these ADSPs 14-20. For example, ADSP #1 14 may miscompare with ADSP #2, 18, but compare favorably with ADSP #4 20. This would be sufficient to declare ADSP #1 14 as not being contaminated.

If, as a result of execution of the air data probe contamination logic 22 by the flight control computer or avionics module 28 on the aircraft 12, it is determined that any one of the four ADSPs 14-20 are assumed to be contaminated, then the flight control computer 28 is notified of this type of problematic condition and the flight control system may take some type of corrective action while the aircraft 12 is still in flight. That is, ruling out even just one of the ADSPs 14-20 as being contaminated is beneficial to the overall FCC or avionics module 28. Also, a notification of this type of problematic condition may be sent as well to the flight crew to alert them to this potentially dangerous condition. This way, a potentially dangerous or even catastrophic situation for the aircraft 12 can be detected and subsequently avoided.

It should be understood that the broadest embodiments of the present invention do not necessarily require that the AOA values from the two vanes 32, 34 be utilized in the air data probe contamination logic 22. However, use of the AOA values from the two vanes in the logic 22 provides for a second "layer" of ADSP 14-20 validation. Thus, as can be seen from the teachings of the foregoing, the broadest embodiments of the present invention comprise an "opposite-side-probe-in-agreement" check, which by itself is sufficient to detect failed (e.g., contaminated) air data sensor probes 14-20.

However, as mentioned hereinabove, alternative embodiments of the present invention may utilize a single vane 32, 34 instead of the two vanes 32, 34 described and illustrated herein. The single vane 32, 34 may be located as shown in FIG. 1 on one side of the aircraft 12. Depending on the level of sensing and logic sophistication of the single vane 32, 34 utilized in these alternative embodiments, one optional embodiment may be to use the actual vane 32, 34 physically located on one side of the aircraft 12 as an extra layer of validation for the ADSPs 14-20 as described hereinabove. At the same time a "dummy" invalid vane may be postulated for the other side of the aircraft 12. Another optional embodiment is to use the actual vane 32, 34 physically located on one side of the aircraft 12 as an extra layer of validation for all of the ADSPs 14-20 if the vane 32, 34 is reasonably compensated for sideslip with the help of other sensors on the aircraft and independent of the air data system. For example, lateral acceleration from inertial sensors located on the aircraft 12 may be used for this compensation task.

Also, it should be understood that the use of four ADSPs 14-20 in the air data probe contamination monitor 22 described and illustrated herein is purely exemplary. Other numbers of ADSPs may be utilized in light of the teachings herein. It suffices that at least two ADSPs 14-20 are used with one of the two ADSPs being located on one side of the aircraft and the other ADSP being located on the other side of the aircraft. This is so as to take "meaningful" data as opposed to "meaningless" data which would comprise similar data from the same side of the aircraft. Along these lines, in alternative embodiments if only two ADSPs 14-20 are utilized—one on each side of the aircraft 12, then only a single additional ADSP 14-20, instead of two additional ADSPs 14-20, may be located on one side of the aircraft 12 and utilized in accordance with the teachings herein.

The use of two separate vanes 32, 34, one mounted on each side of the aircraft 12, has been described and illustrated herein. The vanes 32, 34 have been described and illustrated as being utilized to provide angle of attack ("AOA") values that were then used to determine if any of the ADSPs 14-20 were contaminated. However, in other, alternative embodiments of the present invention, instead of using vanes 32, 34 to provide AOA values, other similar types of vanes may be used to provide angle of sideslip ("AOS") values of the aircraft 12 during flight. A single AOS vane, or a pair of AOS vanes, may be utilized in embodiments of the present invention. An AOS vane may be somewhat physically similar to an AOA vane 32, 34 in that an AOS vane may comprise a relatively small device with a "wing" that aligns itself with the airflow passing by the aircraft.

One primary difference between the AOA vanes 32, 34 previously described and illustrated in FIG. 1 and the AOS vanes is that where the AOA vanes 32, 34 were located on either side of the aircraft 12, the AOS vanes are located on the top and bottom of the aircraft 12—that is, perpendicular to the ground—in order to properly sense the sideslip of the aircraft 12. This can be easily visualized in FIG. 1 by considering the left side of the aircraft 12 shown in that figure as the top of the aircraft 12 and by considering the right side of the aircraft 12 shown in that figure as the bottom of the aircraft 12. If only one AOS vane is utilized in an alternative embodiment, then it may be located on either the top or bottom of the aircraft 12.

Then similar to the logic 22 of FIG. 2 and described hereinabove, the AOS values from the single AOS vane or from the pair of AOS vanes may be utilized to provide a second "layer" of validation. That is, the single AOS vane in an embodiment may be associated with the one or pair of ADSPs 14-20 on one side of the aircraft 12 and a "dummy" invalid AOS vane may be associated with the one or pair of ADSPs 14-20 located on the other side of the aircraft 12. In the alternative, the single AOS vane in an embodiment may be associated with the one or pair of ADSPs 14-20 on one side of the aircraft 12 and that single AOS vane may be reasonably compensated for sideslip with the help of other sensors independent of the air data system on the aircraft 12.

If instead, a pair of AOS vanes are utilized, then the logic 22 of FIG. 2 may be applicable to this alternative embodiment.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more non-transitory computer readable medium(s) having computer readable program code embodied thereon. The computer program product may, for example, be executed by a control system, such as, for example, the flight control computer 28 of FIG. 1.

Any combination of one or more computer readable medium(s) may be utilized. The computer readable medium may be a computer readable signal medium or a non-transitory computer readable storage medium. A non-transitory computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer (e.g., the flight control computer 28 of FIG. 1), other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated herein by reference.

What is claimed is:

1. An air data probe contamination monitor for an aircraft, comprising:
    a flight control computer;
    at least two air data sensor probes, a first one of the probes being located on one side of the aircraft, a second one of the probes being located on an opposite side of the aircraft, each one of the two probes being operable to generate a parameter value from an airflow passing by the aircraft when the aircraft is in flight; and
    a processor that is operable to compare the generated parameter value from the first probe to the generated parameter value from the second probe to determine if one of the first probe and the second probe is contaminated when a difference between the generated parameter from the first probe and the generated parameter from the second probe exceeds a certain value, the processor further being operable to send a notification to the flight control computer of a determination of contamination of the one of the first probe and the second probe.

2. The air data probe contamination monitor of claim 1, wherein the parameter value is generated by sensing an actual pressure from the airflow passing by the aircraft.

3. The air data probe contamination monitor of claim 1, wherein the generated parameter value is an angle of attack value.

4. The air data probe contamination monitor of claim 3, wherein the processor is operable to compare the angle of attack value from the first probe to the angle of attack value from the second probe.

5. The aircraft air data probe contamination monitor of claim 3, further comprising at least two vanes, a first one of the vanes being located on one side of the aircraft, a second one of the vanes being located on an opposite side of the aircraft, each one of the two vanes being operable to generate a parameter value from a direction of an airflow passing by the aircraft when the aircraft is in flight, each of the two vanes also being operable to calculate an angle of attack value from the generated parameter value of the direction of the airflow.

6. The aircraft air data probe contamination monitor of claim 5, wherein the first probe is located on the same side of the aircraft as the first vane, and wherein the second probe is located on the same side of the aircraft as the second vane.

7. The aircraft air data probe contamination monitor of claim 5, wherein the first probe is operable to compare the angle of attack value from the first probe to the angle of attack value from the first vane and to provide a first signal indicative of a result of the first probe/vane comparison, and wherein the second probe is operable to compare the angle of attack value from the second probe to the angle of attack value from the second vane and to provide a second signal indicative of a result of the second probe/vane comparison.

8. The aircraft air data probe contamination monitor of claim 7, wherein the processor is responsive to the first probe/vane comparison signal and is responsive to the second probe/vane comparison signal to determine if either one or both of the first probe and/or the second probe is contaminated.

9. The aircraft air data probe contamination monitor of claim 3, further comprising at least one vane being located on the aircraft and being operable to generate a parameter value from a direction of an airflow passing by the aircraft when the aircraft is in flight, the at least one vane also being operable to calculate an angle of attack value from the generated parameter value of the direction of the airflow.

10. The aircraft air data probe contamination monitor of claim 9, wherein the at least one vane is located on the same side of the aircraft as one of the first and second probes.

11. The aircraft air data probe contamination monitor of claim 9, wherein one of the first probe or second probe is operable to compare the angle of attack value from the at least one vane and to provide a signal indicative of a result of the probe/vane comparison.

12. The aircraft air data probe contamination monitor of claim 11, wherein the processor is responsive to the probe/vane comparison signal to determine if either one or both of the first probe and/or the second probe is contaminated.

13. The air data probe contamination monitor of claim 1, wherein the generated parameter value is an angle of sideslip value.

14. The air data probe contamination monitor of claim 13, wherein the processor is operable to compare the angle of sideslip value from the first probe to the angle of sideslip value from the second probe.

15. The aircraft air data probe contamination monitor of claim 13, further comprising at least one vane being located on the aircraft and being operable to generate a parameter value from a direction of an airflow passing by the aircraft when the aircraft is in flight, the at least one vane also being operable to calculate an angle of sideslip value from the generated parameter value of the direction of the airflow.

16. The aircraft air data probe contamination monitor of claim 15, wherein the at least one vane is located on a top side or a bottom side of the aircraft.

17. The aircraft air data probe contamination monitor of claim 15, wherein one of the first probe or second probe is operable to compare the angle of sideslip value from the at least one vane and to provide a signal indicative of a result of the probe/vane comparison.

18. The aircraft air data probe contamination monitor of claim 17, wherein the processor is responsive to the probe/vane comparison signal to determine if either one or both of the first probe and/or the second probe is contaminated.

19. The aircraft air data probe contamination monitor of claim 13, further comprising at least two vanes, a first one of the vanes being located on a top side of the aircraft, a second one of the vanes being located on a bottom side of the aircraft, each one of the two vanes being operable to generate a parameter value from a direction of an airflow passing by the aircraft when the aircraft is in flight, each of the two vanes also being operable to calculate an angle of sideslip value from the generated parameter value of the direction of the airflow.

20. The aircraft air data probe contamination monitor of claim 19, wherein the first probe is operable to compare the angle of sideslip value from the first probe to the angle of sideslip value from the first vane and to provide a first signal indicative of a result of the first probe/vane comparison, and wherein the second probe is operable to compare the angle of sideslip value from the second probe to the angle of sideslip value from the second vane and to provide a second signal indicative of a result of the second probe/vane comparison.

21. The aircraft air data probe contamination monitor of claim 20, wherein the processor is responsive to the first probe/vane comparison signal and is responsive to the second probe/vane comparison signal to determine if either one or both of the first probe and/or the second probe is contaminated.

22. The aircraft air data probe contamination monitor of claim 1, wherein the air data probe contamination monitor is part of a flight control system for the aircraft.

23. The aircraft air data probe contamination monitor of claim 22, wherein the aircraft flight control system comprises a fly-by-wire type of flight control system.

24. The aircraft air data probe contamination monitor of claim 1, wherein the air data probe contamination monitor is part of a flight control system for the aircraft, and wherein if the processor determines that either one or both of the first probe and/or the second probe is contaminated, then the flight control system is notified of the contaminated first probe and/or second probe and/or a flight crew is notified of the contaminated first probe and/or second probe.

25. The aircraft air data probe contamination monitor of claim 1, further comprising four air data sensor probes, a first two of the probes being located on one side of the aircraft, a second two of the probes being located on an opposite side of the aircraft, each one of the four probes being operable to generate a parameter value from an airflow passing by the aircraft when the aircraft is in flight, each of the four probes also being operable to calculate one of an angle of attack value and an angle of sideslip value each from the generated parameter value.

26. The aircraft air data probe contamination monitor of claim 25, wherein the processor is operable to compare the angle of attack value from each of the first two probes to the angle of attack value from each of the second two probes, and to compare the angle of sideslip value from each of the first two probes to the angle of sideslip value from each of the second two probes to determine if any of the first two probes and/or the second two probes is contaminated.

27. The aircraft air data probe contamination monitor of claim 25, further comprising at least two vanes, a first one of the vanes being located on one side of the aircraft, a second one of the vanes being located on an opposite side of the aircraft, each one of the two vanes being operable to generate a parameter value from a direction of an airflow passing by the aircraft when the aircraft is in flight, each of the two vanes also being operable to calculate an angle of attack value from the generated parameter value, wherein the first two probes are located on the same side of the aircraft as the first vane, and wherein the second two probes are located on the same side of the aircraft as the second vane.

28. The aircraft air data probe contamination monitor of claim 27, wherein each of the first two probes is operable to compare the angle of attack value from each of the first two probes to the angle of attack value from the first vane and to provide a pair of first signals each indicative of a result of the first probe/vane comparison, and wherein each of the second two probes is operable to compare the angle of attack value from each of the second two probes to the angle of attack value from the second vane and to provide a pair of second signals each indicative of a result of the second probe/vane comparison.

29. The aircraft air data probe contamination monitor of claim 28, wherein the processor is responsive to the first pair of probe/vane comparison signals and is responsive to the second pair of probe/vane comparison signals to determine if at least one of the first two probes and/or at least one of the second two probes is contaminated.

30. The aircraft air data probe contamination monitor of claim 1, further comprising a third air data sensor probe, the third probe being located on the same side of the aircraft as either one of the at least two probes, the third probe being operable to generate a parameter value from an airflow passing by the aircraft when the aircraft is in flight, the third probe also being operable to calculate one of an angle of attack value and an angle of sideslip value each from the generated parameter value.

31. The aircraft air data probe contamination monitor of claim 30, wherein the processor is operable to compare the angle of attack value from the third probe to the angle of attack value from the one of the at least two probes located on the opposite side of the aircraft, and to compare the angle of sideslip value from the third probe to the angle of sideslip value from the one of the at least two probes located on the opposite side of the aircraft to determine if any of the first two probes and/or the third probe is contaminated.

32. A method for determining if any one of at least two air data sensor probes mounted on opposite sides of an aircraft is contaminated, the method comprising:
each one of the two probes generating a parameter value from an airflow passing by the aircraft while the aircraft is in flight;
comparing the generated parameter value from the first probe to the generated parameter value from the second probe to determine if one of the first probe and the second probe is contaminated when a difference between the generated parameter from the first probe and the generated parameter from the second probe exceeds a certain value; and
notifying a flight control computer of the aircraft of a determination of contamination of the one of the first probe and the second probe.

33. A computer program product for determining if any one of at least two air data sensor probes mounted on opposite sides of an aircraft is contaminated, the computer program product comprising a non-transitory computer readable storage medium having program code embodied therewith, the program code readable/executable by a computer, processor or logic circuit to perform a method comprising:
each one of the two probes generating a parameter value from an airflow passing by the aircraft while the aircraft is in flight;
comparing the generated parameter value from the first probe to the generated parameter value from the second probe to determine if one of the first probe and the second probe is contaminated when a difference between the generated parameter from the first probe and the generated parameter from the second probe exceeds a certain value; and
notifying a flight control computer of the aircraft of a determination of contamination of the one of the first probe and the second probe.

34. An air data probe contamination monitor for an aircraft, comprising:
at least two air data sensor probes, a first one of the probes being located on one side of the aircraft, a second one of the probes being located on an opposite side of the aircraft, each one of the two probes being operable to generate a parameter value from an airflow passing by the aircraft when the aircraft is in flight;
a vane located on one side of the aircraft and operable to generate a parameter value from airflow passing by the aircraft when the aircraft is in flight; and
a processor that is operable to:
determine agreement of the generated parameter value from the first probe with the generated parameter value from the second probe;
when the generated parameter value from the first probe is not in agreement with the generated parameter value from the second probe, check a signal indicative of whether the generated parameter value of the first probe is in agreement with the generated parameter value of the vane; and
notify a flight control computer of the aircraft of a determination of contamination of one of the first probe and the second probe based on said signal.

* * * * *